(12) United States Patent
Amato et al.

(10) Patent No.: US 8,569,366 B2
(45) Date of Patent: Oct. 29, 2013

(54) ACETYL L-CARNITINE FOR PREVENTION OF PAINFUL PERIPHERAL NEUROPATHY IN PATIENTS WITH TYPE 2 DIABETES

(75) Inventors: Antonino Amato, Gaithersburg, MD (US); Menotti Calvani, Rome (IT)

(73) Assignee: Sigma-Tau Industrie Farmaceutiche Riunite S.p.A., Pomezia (IT)

( * ) Notice: Subject to any disclaimer, the term of this patent is extended or adjusted under 35 U.S.C. 154(b) by 1560 days.

(21) Appl. No.: 11/114,224

(22) Filed: Apr. 26, 2005

(65) Prior Publication Data

US 2006/0241058 A1    Oct. 26, 2006

(51) Int. Cl.
*A61K 31/205*    (2006.01)

(52) U.S. Cl.
USPC ............................ 514/554; 514/555; 514/556

(58) Field of Classification Search
USPC ........................................ 514/556, 554, 555
See application file for complete search history.

(56) References Cited

U.S. PATENT DOCUMENTS 4,751,242 A * 6/1988 Calvani et al. ................ 514/554
2004/0142879 A1* 7/2004 Calvani ........................... 514/23

FOREIGN PATENT DOCUMENTS

EP    0 256 999 A    2/1988

OTHER PUBLICATIONS

Evidentiary Evidence Stedman—paraesthesia.*
Evidentiary Evidence Stedman—diabetes.*
Evidentiary Evidence Webster's—hyperesthesia.*
Merriam-Webster's_eventiary_evidence_preventing.pdf.*
Apr. 1996—Sima, A.A.F. et. al.; Journal of Clinical Investigation; vol. 97, #8, Apr. 1996, 1900-1907.*
Vippagunta (Adv. Drug Del. Rev., 2001, col. 48, 2001, pp. 3-26).*
Grandis De D et al, "L-Acetylcarnitine in the Treatment of Patients with Peripheral Neuropathies . . . ", Clinical Drug Investigation, ADIS International, Auckland, NZ, vol. 10, No. 6, 1995, pp. 317-322; XP001106363.
Quatraro et al, "Acetyl-L-Carnitine for Symptomatic Diabetic Neuropathy", Diabetologia, Berlin, DE, vol. 38, No. 1, 1995, p. 123, XP009050921.

* cited by examiner

*Primary Examiner* — Yong Chong
(74) *Attorney, Agent, or Firm* — Lucas & Mercanti, LLP

(57) ABSTRACT

Acetyl L-carnitine, or of one of its pharmaceutically acceptable salts, is useful for the prevention of painful peripheral neuropathy in patients suffering from type 2 diabetes, in which symptoms are pain, paraesthesia or hyperaesthesia. The acetyl L-carnitine is administered orally at a dose of at least 3 grams/day.

3 Claims, No Drawings

ACETYL L-CARNITINE FOR PREVENTION OF PAINFUL PERIPHERAL NEUROPATHY IN PATIENTS WITH TYPE 2 DIABETES

The present invention relates to the use of acetyl L-carnitine (ALC) for the prevention of painful peripheral neuropathy, characterized by pain, paraesthesia or hyperaesthesia, in patients suffering from type 2 diabetes.

BACKGROUND OF THE INVENTION

Diabetic neuropathy is the most frequent peripheral neuropathy in the western world and includes different forms of neuropathy, the most common of which is diabetic polyneuropathy.

The anatomico-pathological picture of diabetic peripheral neuropathy consists in a focal or widespread non-specific loss of fibers, with demyelination associated with structural or endoneuronal abnormalities of the connective tissue or small vessels.

Various metabolic abnormalities and biochemical changes have been documented both in experimental models of diabetes and in diabetic patients, including an increase in glucose metabolism and a reduction in myoinositol.

The characteristic symptoms of diabetic polyneuropathy include the presence of burning or lancinating pain accompanied by clinical signs of symmetrical impairment of sensitivity, motility, and/or deep tendon reflexes, such symptoms being predominant in the distal segments of the lower limbs.

Diabetic peripheral neuropathy is caused by hyperglycaemia, and metabolic imbalance secondary to hyperglycaemia and ischaemia of the vasa nervorum are the best known pathogenetic mechanisms.

Many variables may speed up or reduce the times when the characteristic symptoms of diabetic peripheral neuropathy in general, and painful peripheral neuropathy in particular, set in; for example, good metabolic control of blood serum glucose levels can certainly delay the onset of these symptoms.

The use of acetyl L-carnitine for the prevention of painful peripheral neuropathy in patients suffering from type 2 diabetes has never been previously described.

In the literature one can find numerous publications that seek to demonstrate or clarify the therapeutic role of acetyl L-carnitine in the treatment of a number of symptoms, including neuropathic pain, in the course of diabetic neuropathy, but these publications do not claim or suggest that acetyl L-carnitine is a useful compound for the prevention of painful peripheral neuropathy in patients suffering from type 2 diabetes.

In Diabetes Care, 2005; Jan.; 28(1): 89-94 it is reported that treatment with ALC is useful for relieving the pain symptoms and for regenerating nerve fibers, in patients suffering from stabilized diabetic neuropathy.

In "Giornale Italiano di Diabetologia, 1998, V. 18, 30-31" the use of acetyl L-carnitine is described for the treatment of neuropathic pain in patients suffering from sensorimotor polyneuropathy.

In Drugs in Research and Development 2002, Vol 3 (4), pp 223-31, the use of acetyl L-carnitine is described for the treatment of neuropathic pain in patients with diabetic neuropathy.

In Diabetologia 1995, VOL/ISS/PG. 38/1 (123) the use of acetyl L-carnitine is described for the treatment of neuropathic pain in patients suffering from diabetic neuropathy.

In "IL GIORNALE DEI CONGRESSI MEDICI, 5, 14-19, 1993" the use of acetyl L-carnitine is described for the treatment of neuropathic pain in patients suffering from diabetic neuropathy on treatment with insulin or oral antidiabetic agents.

In J. of the American Diabetes Association June 2002, Vol 51, Supplement 2, the use of acetyl L-carnitine is described for the treatment of neuropathic pain in patients suffering from diabetic neuropathy.

In CONGRESSO NAZIONALE DELLA SOCIETA ITALIANA DI NEUROFISIOLOGIA CLINICA, ABSTR ACTS, PERUGIA 1-4 Jun., 1994, p 98, the use of acetyl L-carnitine is described for the treatment of neuropathic pain in patients suffering from diabetic neuropathy.

In Clin. Drug. Invest, Vol 10 (6), pp 317-22 1995, the use of acetyl L-carnitine is described for the treatment of neuropathic pain in patients suffering from diabetic neuropathy.

In Int. J. Clin. Pharm. Res. XV(1):9-15; 995, the use of acetyl L-carnitine is described for the treatment of pain in patients suffering from diabetic neuropathy.

In Journal of the Neurological Sciences, 1997, Suppl. to Vol 150 it is reported that acetyl L-carnitine improves nerve conduction velocity in diabetic patients suffering from polyneuropathy.

In IX CONGRESSO NAZIONALE SOCIETA ITALIANA DI FARMACOLOGIA CLINICA; II CONGRESS MEDITERRANEAN SOCIETY CLINICAL PHARMACOLOGY "THERAPEUTIC ADVANCES AND NEW HEALTH PROBLEMS", VENICE, Oct. 8-10, 1991 ABS, the effect of acetyl L-carnitine treatment on 500 patients suffering from peripheral neuropathy of various different origins is described.

In Drugs 1997 September: 54 (3) 414-421 it is reported that acetyl L-carnitine improves nerve conduction velocity in diabetic patients suffering from neuropathy.

U.S. Pat. No. 4,751,242 describes the use of acetyl L-carnitine for the treatment of neuropathic pain in patients with peripheral neuropathy of various origins, including diabetic peripheral neuropathy.

WO 02 096409 refers to the use of acetyl L-carnitine for the preparation of a medicament with "pre-emptive-type" analgesic activity. What is meant by "pre-emptive" analgesia is a therapeutic strategy that involves the early administration of a substance, in relation to the painful event, capable of blocking the entry of the pain stimulus into the central nervous system, thus preventing the facilitating response evoked by the nociceptive impulse to the spinal cord. The efficacy of a "pre-emptive" analgesic drug according to the description in WO 02 096409 depends not only on the time treatment is initiated in relation to the painful event but also on the effective ability of the drug to prevent alterations of central pain sensitization mechanisms.

WO 02 096409, as an example of preventive pain therapy, indicates the prevention of pain that occurs after a surgical operation.

In these studies, there is never any description or suggestion of the use of ALC for the prevention of painful peripheral neuropathy in patients suffering from type 2 diabetes.

In the medical field no drugs are known which are useful for the prevention of painful peripheral neuropathy in patients suffering from type 2 diabetes.

DESCRIPTION OF THE INVENTION

It has now been found that acetyl L-carnitine is a useful agent for the prevention of painful peripheral neuropathy in patients suffering from type 2 diabetes.

The object of the present invention is therefore the use of acetyl L-carnitine (ALC), or one of its pharmaceutically acceptable salts, for the prevention of painful peripheral neuropathy in patients suffering from type 2 diabetes, in which the painful peripheral neuropathy is characterized by symptoms of pain, paraesthesia and/or hyperaesthesia.

What is meant by pharmaceutically acceptable salt of acetyl L-carnitine is any salt of the latter with an acid that does not give rise to unwanted toxic effects. These acids are well known to pharmacologists and to experts in pharmaceutical technology.

Non-limiting examples of such salts are, for example, chloride, bromide, orotate, acid aspartate, acid citrate, magnesium citrate, acid phosphate, fumarate and acid fumarate, magnesium fumarate, lactate, maleate and acid maleate, mucate, acid oxalate, pamoate, acid pamoate, acid sulphate, glucose phosphate, tartrate, acid tartrate, magnesium tartrate, 2-amino ethanesulphonate, magnesium 2-amino ethanesulphonate, choline tartrate and trichloroacetate.

The following examples illustrate the invention.

EXAMPLE 1

Clinical Trial BM 14329

A multicenter, randomized, double-blind, placebo-controlled clinical trial of 52 weeks' duration was conducted in patients with type 2 diabetes suffering from diabetic peripheral neuropathy.

The patients were treated with acetyl L-carnitine at a dose of 0.5 grams or 1 gram, three times daily, or with placebo for 52 weeks.

The patients recruited into the trial were patients of male and female sex and were aged from 18 to 70 years, in whom diabetes had been diagnosed more than one year earlier and presenting HbAlc greater than 5.9%.

After 12, 26 and 52 weeks of treatment, the presence and intensity of pain, paraesthesia and hyperaesthesia, among other variables, were assessed as characteristic symptoms of painful peripheral neuropathy in patients who at the time of recruitment presented no such symptoms.

At the end of the clinical trial, statistical analysis of the results obtained showed that treatment with ALC for 26 or 52 weeks was capable of treating and relieving the symptoms of diabetic peripheral neuropathy that were already present at the start of the clinical trial. The curative effect was not the same in all the population treated, but was better only in patients with type 2 diabetes.

Further processing of the experimental data in this clinical trial showed, unexpectedly and surprisingly, that acetyl L-carnitine was capable not only of treating or ameliorating but also of preventing the symptoms typical of diabetic painful peripheral neuropathy, including pain, hyperaesthesia and paraesthesia, in patients who at entry into the trial did not present such symptoms.

Even more surprising was the discovery that this preventive activity was present only in patients suffering from type 2 diabetes and at the higher dose of the drug administered.

The results in patients with type 2 diabetes treated with ALC at the dose of 3 grams/day are reported in Tables 1-3 here below.

TABLE 1

| | Placebo (n = 152 patients) | | Acetyl L-carnitine 3.0 g/day (n = 217 patients) | | Significance (P value, Fisher Exact Test) Placebo |
|---|---|---|---|---|---|
| Symptom | Basal | 12 weeks | Basal | 12 weeks | vs ALC |
| Pain | 0% | 27.0% | 0% | 17.1% | 0.027 |
| Pain, hyperaesthesia, paraesthesia | 0% | 50.0% | 0% | 35.5% | 0.007 |

TABLE 2

| | Placebo (n = 152 patients) | | Acetyl L-carnitine 3.0 g/day (n = 217 patients) | | Significance (P value, Fisher Exact Test) Placebo |
|---|---|---|---|---|---|
| Symptom | Basal | 26 weeks | Basal | 26 weeks | vs ALC |
| Pain | 0% | 27.0% | 0% | 20.3% | 0.11 |
| Pain, hyperaesthesia, paraesthesia | 0% | 51.6% | 0% | 38.6% | 0.007 |

TABLE 3

| | Placebo (n = 152 patients) | | Acetyl L-carnitine 3.0 g/day (n = 217 patients) | | Significance (P value, Fisher Exact Test) Placebo |
|---|---|---|---|---|---|
| Symptom | Basal | 52 weeks | Basal | 52 weeks | vs ALC |
| Pain | 0% | 32.9% | 0% | 29.5% | 0.494 |
| Pain, hyperaesthesia paraesthesia | 0% | 59.2% | 0% | 47.5% | 0.027 |

EXAMPLE 2

Clinical Trial BM 14330

A multicenter randomized, double-blind, placebo-controlled clinical trial was conducted with the same characteristics as the clinical trial described in Example 1.

The results obtained in patients with type 2 diabetes treated with ALC at the dose of 3 grams/day, are reported in Tables 4-6 here below.

TABLE 4

| | Placebo (n = 142 patients) | | Acetyl L-carnitine 3.0 g/day (n = 181 patients) | | Significance (P value, Fisher Exact Test) |
|---|---|---|---|---|---|
| Symptom | Basal | 12 weeks | Basal | 12 weeks | Placebo vs ALC |
| Pain | 0% | 45.1% | 0% | 27.6% | 0.001 |
| Pain, hyperaesthesia, paraesthesia | 0% | 64.1% | 0% | 42.5% | 0.001 |

TABLE 5

| Symptom | Placebo (n = 142 patients) | | Acetyl L-carnitine 3.0 g/day (n = 181 patients) | | Significance (Fisher Exact Test) Placebo vs ALC |
|---|---|---|---|---|---|
| | Basal | 12 weeks | Basal | 12 weeks | |
| Pain | 0% | 45.8% | 0% | 28.7% | 0.002 |
| Pain, hyper-aesthesia, paraesthesia | 0% | 64.8% | 0% | 43.1% | 0.001 |

TABLE 6

| Symptom | Placebo (n = 142 patients) | | Acetyl L-carnitine 3.0 g/day (n = 181 patients) | | Significance (P value, Fisher Exact Test) Placebo vs ALC |
|---|---|---|---|---|---|
| | Basal | 52 weeks | Basal | 52 weeks | |
| Pain | 0% | 54.9% | 0% | 35.9% | 0.001 |
| Pain, hyper-aesthesia, paraesthesia | 0% | 66.9% | 0% | 48.1% | 0.001 |

On analyzing the results reported in Tables 1-6, it will be noted that the use of ALC showed a statistically significant ability to prevent the onset of symptoms associated with diabetic painful peripheral neuropathy, such as pain, paraesthesia and hyperaesthesia.

Acetyl L-carnitine is a known compound, whose preparation process is described in U.S. Pat. Nos. 4,439,438 and 4,254,053.

The acetyl L-carnitine can be in any form suitable for oral or parenteral administration in human subjects.

On the basis of various factors such as the concentration of active ingredient and the patient's condition, the ALC can be prepared as a health food supplement, nutritional supplement, or as a therapeutic product on sale subject to obtaining a doctor's prescription or without a doctor's prescription.

It has been found that, though the daily dose of the above-mentioned active ingredient to be administered depends on the patient's age, weight and general condition, on the basis of professional experience, for the prevention of diabetic painful peripheral neuropathy in patients with type 2 diabetes, it is necessary to administer, in multiple doses, an amount of ALC corresponding to at least 3 grams a day, or an equimolar amount of one of its pharmaceutically acceptable salts.

The medicament according to the present invention can be prepared by mixing the active ingredient (acetyl L-carnitine inner salt or one of its pharmaceutically acceptable salts) with excipients suitable for the formulation of compositions for enteral (particularly oral) or parenteral (particularly intramuscular or intravenous) administration. Such excipients are well known to experts in pharmaceutical technology.

The pharmaceutically acceptable salts of the above-mentioned active ingredients include all pharmaceutically acceptable salts that are prepared by addition of an acid to acetyl L-carnitine inner salt, and that do not give rise to unwanted toxic or side effects. The formation of salts by addition of acids is a well known practice in pharmaceutical technology.

The invention claimed is:

1. A method for treating and relieving symptoms of diabetic neuropathy in patients affected by type 2 diabetes, comprising administering to a patient in need thereof 3 grams/day of acetyl L-carnitine, or a pharmaceutically acceptable salt thereof for at least 52 weeks in which said symptoms are selected from the group consisting of pain, paraesthesia or hyperaesthesia.

2. The method according to claim 1, in which the pharmaceutically acceptable salt of acetyl L-carnitine is selected from the group consisting of chloride, bromide, orotate, acid aspartate, acid citrate, magnesium citrate, acid phosphate, fumarate and acid fumarate, magnesium fumarate, lactate, maleate and acid maleate, mucate, acid oxalate, pamoate, acid pamoate, acid sulphate, glucose, phosphate, tartrate, acid tartrate, magnesium tartrate, 2-aminoethansulphonate, magnesium 2-ethansulphonate, choline tartrate and trichloroacetate.

3. The method according to claim 1, in which the pharmaceutically acceptable salt of acetyl L-carnitine is a chloride salt.

* * * * *